United States Patent
Do et al.

(10) Patent No.: US 11,083,363 B2
(45) Date of Patent: Aug. 10, 2021

(54) ENDOSCOPE CONTROL DEVICE AND ENDOSCOPE

(71) Applicant: DIGITAL ENDOSCOPY GMBH, Friedberg (DE)

(72) Inventors: Anh Minh Do, Munich (DE); Joachim Axel Fett, Augsburg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 248 days.

(21) Appl. No.: 16/089,690

(22) PCT Filed: Mar. 28, 2017

(86) PCT No.: PCT/EP2017/057249
§ 371 (c)(1),
(2) Date: Sep. 28, 2018

(87) PCT Pub. No.: WO2017/167713
PCT Pub. Date: Oct. 5, 2017

(65) Prior Publication Data
US 2019/0110661 A1 Apr. 18, 2019

(30) Foreign Application Priority Data
Mar. 30, 2016 (DE) ...................... 10 2016 105 767.3

(51) Int. Cl.
*A61B 1/00* (2006.01)
*A61B 1/005* (2006.01)
*A61B 1/01* (2006.01)

(52) U.S. Cl.
CPC .......... *A61B 1/0052* (2013.01); *A61B 1/0057* (2013.01); *A61B 1/00154* (2013.01); *A61B 1/01* (2013.01)

(58) Field of Classification Search
CPC . A61B 1/0052; A61B 1/0057; A61B 1/00154; A61B 1/01; A61B 2034/715;
(Continued)

(56) References Cited

U.S. PATENT DOCUMENTS

| 3,892,228 A | 7/1975 | Mitsui |
| 4,941,454 A | 7/1990 | Wood et al. |

(Continued)

FOREIGN PATENT DOCUMENTS

| DE | 2 350 382 B2 | 4/1974 |
| EP | 1 886 617 A1 | 2/2008 |

(Continued)

OTHER PUBLICATIONS

International Search Report issued in International Bureau of WIPO Patent Application No. PCT/EP2017/057249, dated Jun. 6, 2017.
(Continued)

*Primary Examiner* — Timothy J Neal
*Assistant Examiner* — Sung Ham
(74) *Attorney, Agent, or Firm* — Greenblum & Bernstein, P.L.C.

(57) ABSTRACT

The invention relates to an endoscope control device for a non-rigid endoscope, including a tiltable control element for effecting a deflection movement by means of a transmission wire, the control element including a wire guiding means for guiding a wire; the wire, which is arranged at the control element on the wire guiding means for realizing the deflection movement; and a wire tensioning body in which a proximal end of the wire is anchored and which is movable relative to the control element for changing the tension of the wire between the wire guiding means and the wire tensioning body.

12 Claims, 22 Drawing Sheets

(58) Field of Classification Search
CPC .... A61B 34/71; Y10T 74/20408; G05G 9/047
USPC .................................................. 600/146, 149
See application file for complete search history.

(56) References Cited

U.S. PATENT DOCUMENTS

| | | | |
|---|---|---|---|
| 5,960,145 A * | 9/1999 | Sanchez | G02B 23/26 |
| | | | 385/115 |
| 6,440,062 B1 | 8/2002 | Ouchi | |
| 8,801,752 B2 * | 8/2014 | Fortier | A61B 17/29 |
| | | | 606/205 |
| 10,092,171 B2 | 10/2018 | Viebach et al. | |
| 2007/0221701 A1 * | 9/2007 | Ortiz | A61B 1/0052 |
| | | | 227/175.1 |
| 2008/0255421 A1 * | 10/2008 | Hegeman | A61B 1/0055 |
| | | | 600/139 |
| 2009/0209820 A1 | 8/2009 | Tanaka | |
| 2009/0287188 A1 * | 11/2009 | Golden | A61M 25/0147 |
| | | | 604/528 |
| 2009/0299344 A1 | 12/2009 | Lee et al. | |
| 2012/0302832 A1 * | 11/2012 | Inada | A61B 1/00039 |
| | | | 600/118 |
| 2014/0148646 A1 | 5/2014 | Inada | |
| 2015/0366435 A1 | 12/2015 | Williams | |
| 2016/0278616 A1 | 9/2016 | Viebach et al. | |
| 2016/0341241 A1 * | 11/2016 | Hosaka | F16C 1/12 |
| 2018/0160883 A1 | 6/2018 | Viebach et al. | |

FOREIGN PATENT DOCUMENTS

| | | |
|---|---|---|
| EP | 2 740 397 A1 | 6/2014 |
| WO | 2015/063052 A1 | 5/2015 |

OTHER PUBLICATIONS

Office Action issued in German family member Patent Appl. No. 10 2016 105 767.3, dated Feb. 24, 2017.

* cited by examiner

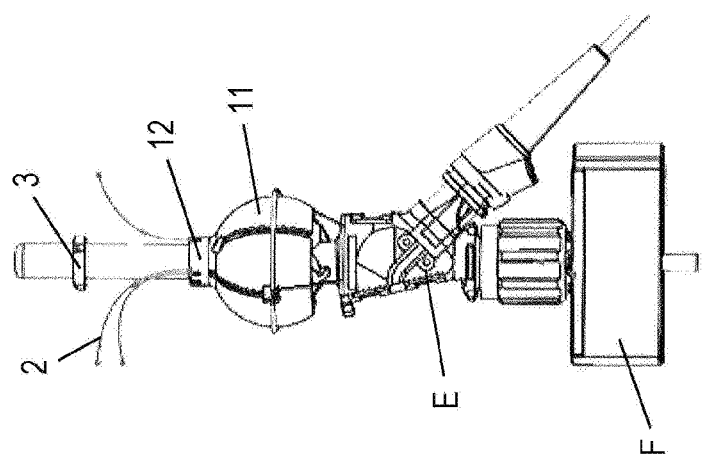

ENDOSCOPE CONTROL DEVICE AND ENDOSCOPE

The present invention relates to an endoscope control device for a non-rigid endoscope and to an endoscope comprising such an endoscope control device.

In medical examinations with non-rigid endoscopes, a tilting movement of a control element is transformed into a deflection movement (bending movement) of a deflecting member or deflecting portion by means of a deflection movement transmitting means. For operation by the user, the control element is usually arranged on the proximal side of the endoscope so as to be operated by the user. The deflecting member (deflecting portion) is usually arranged on the distal side of the endoscope and is bent, i.e. deflected, by the user in the desired manner. The transmission of the deflection movement takes place from the control element to the deflecting member (deflecting portion) via control wires (pulling cables).

The transmission of the deflection movement takes place over the entire length of the endoscope. For this, the pulling cables are pulled with enormous forces and therefore have to be appropriately attached to the control element.

OBJECT UNDERLYING THE INVENTION

It is the object of the present invention to provide an improved endoscope control device and an improved endoscope, where the control wires (pulling cables) of the deflection movement transmitting means are advantageously fixed.

Solution to the Problem

This problem is solved by an endoscope control device. An endoscope is shown herein. Further advantageous developments are disclosed herein.

Hence, an endoscope control device for a non-rigid endoscope has been provided, the endoscope control device comprising a tiltable control element for effecting a deflection movement by means of a transmission wire, the control element including a wire guiding means for guiding a wire; the wire which is arranged at the control element on the wire guiding means for realizing the deflection movement; and a wire tensioning body in which a proximal end of the wire is anchored and which is movable relative to the control element for changing the tension of the wire between the wire guiding means and the wire tensioning body.

In the endoscope control device according to the invention, the tension of the transmission wire between the wire guiding means and the wire tensioning body can be changed by means of the wire tensioning body. The transmission wire which transmits the user's control movement of the tiltable control element to a distal deflecting member or deflecting portion of an endoscope can thus be appropriately and specifically tensioned. Thus, an improved, easy to handle fixing construction of the transmission wire for an endoscope control device has been provided.

The wire tensioning body in which a proximal end of the wire is anchored, is moved relative to the control element in order to tension the transmission wire.

This tensioning of the transmission wire can be a retensioning of an already tensioned transmission wire. Alternatively, this tensioning of the transmission wire can be a first tensioning of the transmission wire. In the latter case, it is possible in such an endoscope control device that the pulling cables attached to the deflection movement transmitting means are activated and tensioned only by the end-user.

The advantage of the wire being tensioned only by the end-user is that the system can be stored over a long period of time without a loss of functionality. If the system was under tension right from the beginning, this tension would have a negative effect on the quality of the system due to material fatigue. Therefore, the endoscope control device according to the invention has a longer service life than conventional systems. Moreover, the actual start of the service life is that point in time when the wire is tensioned for the first time. Thus, the start of the service life can be determined by the end-user himself.

Further, the endoscope control device according to the invention makes it possible to assemble and store an endoscope comprising this endoscope control device under untensioned conditions.

The wire tensioning body can be movable relative to the control element such that a predefined tension can be applied to the wire. The wire tensioning body is movable relative to the control element by a predetermined movement path or angle such that the desired optimum tension of the transmission wire is achieved.

The wire tensioning body can be rotatable relative to the control element such that the predefined tension can be applied to the wire.

This predefined tension of the wire is achieved by a rotational movement of the deflection movement transmitting means, which leads directly to an extension of the distance and, thus, to a tension of the attached wire.

The endoscope control device can comprise an engagement member which engages at a predefined movement length of the wire, effected by a movement of the wire tensioning body. Alternatively, the endoscope control device can comprise multiple engagement members which engage at a predefined movement length of the wire, effected by a movement of the wire tensioning body. Such an endoscope control device makes it possible to maintain the desired predefined tension of the wire tensioning body after the wire has been tensioned.

The engagement member can be designed to be engageable such that the engagement is irreversible. This is advantageous, particularly for the first tensioning of the wire tensioning body. The wire tension of the wire tensioning body to be achieved is structurally predefined and can be induced shortly before the application of the endoscope by the user himself by operating the wire tensioning body. Thereby, an endoscope comprising this endoscope control device can be stored relatively long in a state of untensioned wires, and can be made ready for immediate use by an easily performable action. Then, once the wire is tensioned, the user cannot independently change the tension of the wire. This has the effect that a user cannot tension the wire in a manner not desired by the manufacturer. In this way, an incorrect tension of the wire by the user—too strong or too weak—can be avoided. Such an endoscope control device is especially suitable for single uses in which a possible reduction in the tension of the wire is insignificant.

On the other hand, the engagement member can be designed to be engageable such that the engagement can be released. Alternatively, the engagement members can be designed to be engageable such that the engagement can be released.

The user himself can release the tension state of the tensioned wires again and reset the wires in the untensioned state by moving back the wire tensioning body. Such an endoscope control device is e.g. particularly suitable for applications in which a possible reduction of the tension of the wire is to be prevented. Here, the user can tension the initially untensioned wires immediately before using the endoscope. After the use of the endoscope, the user can release the wires again. Thus, the endoscope can be cleaned, sterilized and stored in a state of untensioned wires until it is used again.

The wire tensioning body can be arranged on the proximal side of the control element. Thereby, the wire tensioning body is easily accessible to the user and simple to handle. For example, the wires can be tensioned by a simple movement of the thumb and the index finger on the wire tensioning body.

The wire tensioning body can be an annular body having wire anchoring openings in which the wire is placed, wherein, for tensioning the wire, the annular body is rotatable relative to the control element. In this way, the tensioning of the wires can be achieved by an easily performable rotational movement of the wire tensioning body.

The annular body can be arranged with respect to the control element such that a proximal surface of the annular body faces away from the control element and a distal surface of the annular body faces towards the control element. The wire anchoring openings can be through-holes between the proximal surface and the distal surface of the annular body. The proximal end of the wire for anchoring can be wound along a first wire anchoring opening, a portion of the proximal surface of the annular body, a second wire anchoring opening and a portion of the distal surface of the annular body.

In the wire tensioning body, at least two wires can be anchored in the wire anchoring openings such that the at least two wires have tensionable lengths differently long to each other between their respective anchoring site on the wire tensioning body and their respective wire guiding means of the control element, wherein, during a movement of the wire tensioning body relative to the wire guiding means of the control element, the at least two anchored wires are tensionable at changes in length which are different from each other.

Thus, by attaching the pulling cables to different positions with respect to the rotating movement of the deflection movement transmitting means, each fitted wire can experience a change in length different from another wire and, thus, a tension. This enables the user of an endoscope to adjust the tension of the wires individually and separately as needed.

Further, the endoscope control device can comprise a fixing member for temporarily fixing the wire independently of the wire tensioning body. Thus, the endoscope control device according to the invention makes it possible that the members which tension the wire are not affected by those members used for a treatment-related temporary fixing of the wire by which a specific achieved deflection position of the deflecting member (deflecting portion) is fixed, and vice versa.

The features discussed above may be combined in any manner.

BRIEF DESCRIPTION OF THE DRAWINGS

FIG. 14 shows a side view of a basic endoscope with the mounted tilting body 11 and the assembly pin D and the wire tensioning body 3.

FIG. 15 shows a perspective view of the assembly pin D and the wire tensioning body 3 and the engagement member 4.

EMBODIMENTS

First Embodiment

Subsequently, a first embodiment of the present invention is described by means of the attached drawings.

Figure 1:
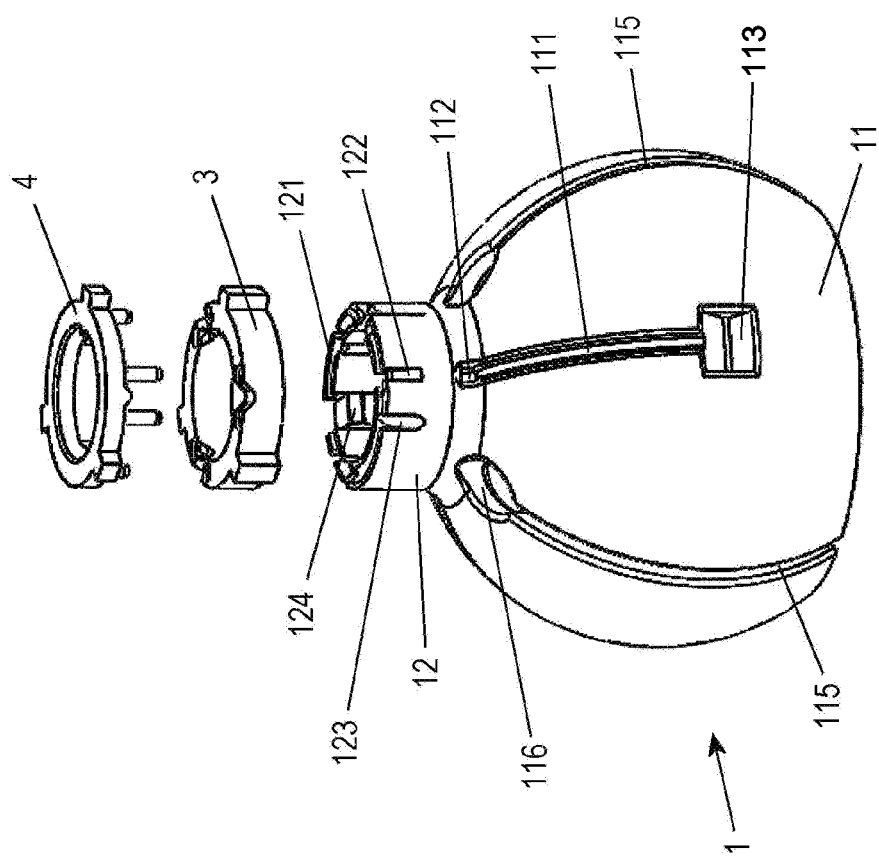
FIG. 1 shows a perspective exploded view of a control element 1 as an endoscope control device of the first embodiment of the present invention.

FIG. 1 shows a control element 1 of an endoscope control device of the embodiment of the present invention, comprising a tilting body 11, an annular extension 12, a wire tensioning body 3 and an engagement member 4. The tilting body 11 and the annular extension 12 are designed integrally, the tilting body 11 being arranged on the distal side and the annular extension 12 being arranged on the proximal side. Thus, the annular extension 12 forms a proximal extension of the tilting body 11. In FIG. 1, the upward direction is the proximal direction facing towards the user, while the downward direction is the distal direction facing away from the user.

Structure for Accomplishing the Wire Tensioning

The structure for accomplishing the tensioning of the wire is described in the following.

Base Member Consisting of the Tilting Body 11 with the Annular Extension 12

Together with the annular extension 12, the tilting body 11 is made of a plastic material. An injection molding method can be applied, for example, but the invention is not restricted thereto. The tilting body 11 is a spherical joystick element as shown in FIG. 1. The tilting body 11 is seated on a head not shown in FIG. 1. In particular, the tilting body 11 forms a hollow ball portion of the endoscope control device 1 according to the invention, wherein this hollow ball portion is seated on a counter ball portion (counter ball segment) which forms the above-mentioned head but is not shown in FIG. 1. The counter ball portion is formed in such a manner that it has a ball shape of such a size that the tilting body 11 placed thereon is smoothly movable. The relation of dimensions between the counter ball portion and the tilting body 11 is such that a movement of the tilting body 11 relative to the counter ball portion is possible without any great effort by the user, while, on the other hand, the tilting body 11 is not placed loosely on the counter pall portion. Thus, the control element 1 can tilt as a joystick relative to the counter ball portion for effecting a deflection movement by means of a transmission wire not shown in FIG. 1. The tilting body 11 has an opening at the pole region. The annular extension 12 is located at the pole of the tilting body 11.

In a schematic perspective extract-like representation, FIG. 1 shows details of the connection of the wires to the control element 1. So as to improve clarity, the subsequently discussed wires have been omitted in FIG. 1.

As it is shown in FIG. 1, the outer circumferential surface of the tilting body 11 is provided with three bottomed grooves 111 as wire guiding means, of which only one groove 111 is shown in FIG. 1. The three grooves 111 are arranged symmetrically and equally spaced apart at the outer circumferential surface of the tilting body 11. Each groove 111 extends downwards, i.e. in the distal direction, from below the transition to the annular extension 12, to beyond an equatorial line at the tilting body 11. In particular, each groove 111 extends on the outer surface of the tilting body 11 from a top opening 112 to a bottom opening 113. The top opening 112 forms a proximal opening and the bottom opening 113 forms a distal opening.

The proximal opening 112 is formed as through-opening penetrating the hollow ball shape of the tilting body 11. The distal opening 113 is designed as blind hole on the outer surface of the tilting body 11. Thus, the groove 111 passes into a through bore at the proximal opening 112. The groove 111 serves as wire guiding means, the wire being arranged in the groove 111 such that, the wire coming from the distal side and passing the distal opening 113 is placed in the bottomed groove 111 at the outer side of the tilting body 11 and is guided from the outside to the inner circumferential side of the tilting body 11 through the proximal opening 112. Therefore, when it is tightened, the wire abuts against the bottom of the groove 111 between the proximal opening 112 and the distal opening 113.

In addition to the grooves 111, three incisions 115 are provided at the outer circumferential surface of the tilting body 11, of which only two incisions 115 are shown in FIG. 1. Each of the three incisions 115 is arranged symmetrically and equally spaced apart at the outer circumferential surface of the tilting body 11 between two grooves 111. Each incision 115 extends upwards, i.e. in the proximal direction, from the bottom end of the tilting body 11 to below the transition to the annular extension 12. Each incision 115 forms a gap having a constant width. Due to the incisions 115, the elastic tilting body 11 can be bent open and can be placed on the counter ball portion.

An end portion 116 is provided at the proximal end of the incision 115. The width of the end portion 116 in the latitude direction is larger than the width of the incision 115.

Hence, the grooves 111 and the incisions 115 are provided at the outer circumferential surface in the meridian direction of the tilting body 11. The number of grooves 111 and incisions 115 is not restricted. The number of grooves 111 depends on the number of wires used. The number of grooves 111 may differ from the number of incisions 115.

The annular extension 12 is formed as a hollow ring body. The annular extension 12 has an inner circumferential surface, an outer circumferential surface, a distal surface facing toward the tilting body 11 and a proximal surface facing away from the tilting body 11. The annular extension 12 is integrally arranged at a pole of the tilting body 11. The annular extension 12 surrounds the proximal opening of the tilting body 11, formed at the pole of the tilting body 11.

At the proximal surface, the annular extension 12 has a channel 121 extending in a circumferential direction, which may be interrupted in the circumferential direction as FIG. 1 shows. On both the outer circumferential surface and the inner circumferential surface the channel 121 is surrounded by a wall.

Furthermore, on the proximal side of the annular extension 12, a respective wire inlet slit 122 extending in the axial direction is provided at a position corresponding to an extension of the respective groove 111. Thus, on the proximal side of the annular extension 12, three wire inlet slits 122 are formed spaced apart by 120°. Such a wire inlet slit 122 allows a wire passing along the inner circumferential surface of the annular extension 12 above the proximal opening 112 to be inserted radially obliquely to the outside into the wire inlet slit 122 and into a subsequently explained corresponding through-opening 31 of the wire tensioning body 3.

Figure 2:
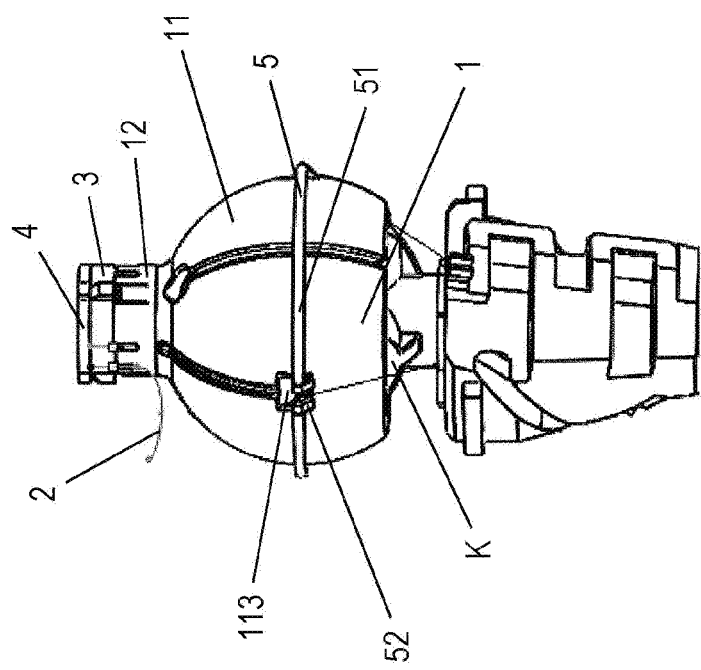
FIG. 2 shows a side view of the endoscope control device of the first embodiment.

Moreover, on the proximal side of the annular extension 12, a respective wire outlet slit 123 extending in the axial direction is provided at a position spaced apart from the wire inlet slit 122 in the circumferential direction. Thus, three wire outlet slits 123 spaced apart by 120° are formed on the proximal side of the annular extension 12. Such a wire outlet slit 123 enables a wire end leaving the subsequently described wire tensioning body 3 to get to the outside through the wire outlet slit 123, as it is shown in FIG. 2.

A first latching nose 124 for a subsequently described covering body, extending radially inwards is provided at the inner circumferential surface of the annular extension 12, wherein the covering body covers the control element 1 from the proximal side. A further radially inwardly extending latching nose (not shown) is also arranged on the inner circumferential surface of the annular extension 12 on the same level as the first latching nose 124 and offset by approx. 120° with respect to the first latching nose 124.

Wire Tensioning Body 3

The wire tensioning body 3 forms an annular body and is made of a plastic material, but can alternatively be made of a metal as well. Thus, the wire tensioning body 3 has an inner circumferential surface, an outer circumferential surface, a distal surface facing towards the tilting body 11 and a proximal surface facing away from the tilting body 11. In the wire tensioning body 3, through-openings 31 formed as pairs are provided in the axial direction as wire anchoring openings between the distal surface and the proximal surface. In the embodiment, three pairs of through-openings 31 are provided, each pair being assigned to one wire, and thus, to one groove 111 of the tilting body 11. Hence, the respective pairs of through-openings 31 are arranged symmetrically and equally spaced apart on the wire tensioning body 3. Incidentally, the through-openings 31 are arranged radially offset from the inner circumferential surface and the outer circumferential surface of the wire tensioning body 3. The through-openings 31 belonging to a pair of through-openings 31 are spaced apart in the circumferential direction of the wire tensioning body 3. The distance of the through openings 31 belonging to a pair of through-openings 31 corresponds to the distance between the wire inlet slit 122 and the wire outlet slit 123 in the circumferential direction of the annular extension 12.

Between each two through-openings 31 forming a pair, there is a center at which a notch 32 is provided on the proximal surface. In this way, there are three notches 32 which are spaced apart from each other by 120° in the embodiment.

Figure 3:
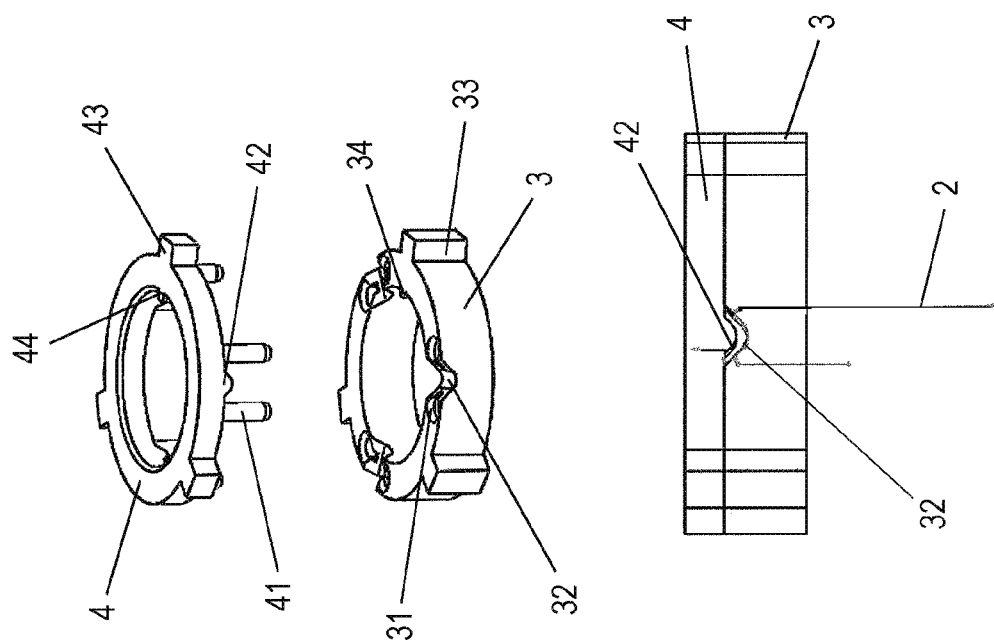
FIG. 3 shows the fixing of a wire; the upper part of FIG. 3 shows an engagement member 4, the middle part of FIG. 3 shows a wire tensioning body 3 having a wire 2, and the lower part of FIG. 3 shows how the wire tensioning body 3 and the engagement member 4 are assembled.

On the outer circumferential surface, the wire tensioning body 3 has axially extending protrusions 33 in a cuboid-like shape, as it is shown in FIG. 3. The protrusions 33 are also arranged symmetrically and equally spaced apart on the wire tensioning body 3. In the embodiment, the protrusions 33 are provided between the notches 32, viewed in the circumferential direction of the wire tensioning body 3. The wire tensioning body 3 has an axially extending nose 34 on the inner circumferential surface. Three protrusions 33 are provided in the embodiment, but the invention is not restricted to a certain number of protrusions.

Engagement Member 4

The engagement member 4 is formed in an annular shape. The engagement member 4 is made of a plastic material but may alternatively also be made of a metal. The engagement member 4 has an inner circumferential surface, an outer circumferential surface, a distal surface facing towards the wire tensioning body 3 and a proximal surface facing away from the wire tensioning body 3. Locking pins 41 protruding in the axial direction and formed as pairs are provided on the distal surface. Each locking pin 41 is arranged on the distal surface of the engagement member 4 and dimensioned such that it can be inserted into one through-opening 31. Therefore, three pairs of locking pins 41 are provided in the embodiment, each of the pairs being assigned to one wire. The respective pairs of locking pins 41 are therefore arranged symmetrically and spaced apart by 120° on the engagement member 4.

Bulges 42 protruding in the axial direction are provided on the distal surface of the engagement member 4, the bulges having a shorter axial length than the locking pins 41. In the embodiment, three bulges 42 are provided of which only one bulge 42 is shown in FIG. 3. The bulges 42 are arranged symmetrically and equally spaced apart by 120° and offset on the engagement member 4. In the embodiment, one bulge 42 is provided between each of the pairs of locking pins 41. When the engagement member 4 is placed on the wire tensioning body 3, each bulge 42 engages into one corresponding notch 32.

On the outer circumferential surface the engagement member 4 has axially extending protrusions 43 in a cuboid-like shape. The protrusions 43 are also arranged symmetrically and equally spaced apart on the engagement member 4. In the embodiment, regarding the shape, the arrangement and the alignment, the protrusions 43 are arranged on the engagement member 4 in a manner corresponding to the protrusions 33 of the wire tensioning body 3, cf. also shown in FIG. 3.

The engagement member 4 has an axially extending nose 44 on the inner circumferential surface.

Fixing of the Wire 2

For the wire tensioning body 3 being able to tension the wire 2, the wire 2 has to be fixedly anchored, i.e. fixed in the wire tensioning body.

In the following, the fixing of the wire 2 in the wire tensioning body 3 is explained in more detail by referring to FIG. 3. Here, it has to be noted that there are multiple possibilities of fixing the wire 2 to the assembly composed of the wire tensioning body 3 and the engagement member 4.

FIG. 3 shows the fixing of a wire, an engagement member 4, a wire tensioning body 3 with a wire 2, and how the wire tensioning body 3 and the engagement member 4 are assembled to fix the wire 2.

In the present embodiment, the wire 2 is inserted in a first pair of through-openings 31 from the distal side of the wire tensioning body 3, passes through the first through-opening 31 in the proximal direction and is inserted into the second through-opening 31 on the proximal side of the wire tensioning body 3 and passes through the second through-opening 31 in the distal direction, as it is shown in FIG. 3.

In this state, the engagement member 4 is arranged from the proximal side on the wire tensioning body 3 provided with the wire 2 so that the respective locking pin 41 is inserted into its corresponding through-opening 31, cf. FIG. 3. Thus, the locking pin 41 clamps the wire 2 positioned in its corresponding through-opening 31. When, in the state shown in FIG. 3, the engagement member 4 is further pushed in the distal direction, the bulge 42 enters the notch 32 and tensions the portion of the wire on the proximal side of the wire tensioning body 3. In this way, a sufficient static friction of the wire 2 is realized at three positions at the same time: between one locking pin 41 and its corresponding through-opening 31; between the bulge 42 and the notch 32; and between another locking pin 41 and its corresponding through-opening 31.

In FIG. 3 the wire 2 is thus anchored to the wire tensioning body 3 and the engagement member 4 by means of a loop. Such a clamping of the wire 2 in the wire tensioning body 3 and the engagement member 4 already ensures a sufficient fixing of the wire 2. Of course, the wire 2 can also be fixed such that it is anchored in two or more loops to the wire tensioning body 3 and the engagement member 4. This means, after the wire 2 has left the second through-opening 31, it is again inserted into the first pair of through-openings 31 in the proximal direction, passes the same, and so on.

Tensioning of the Wire 2

Figure 4:
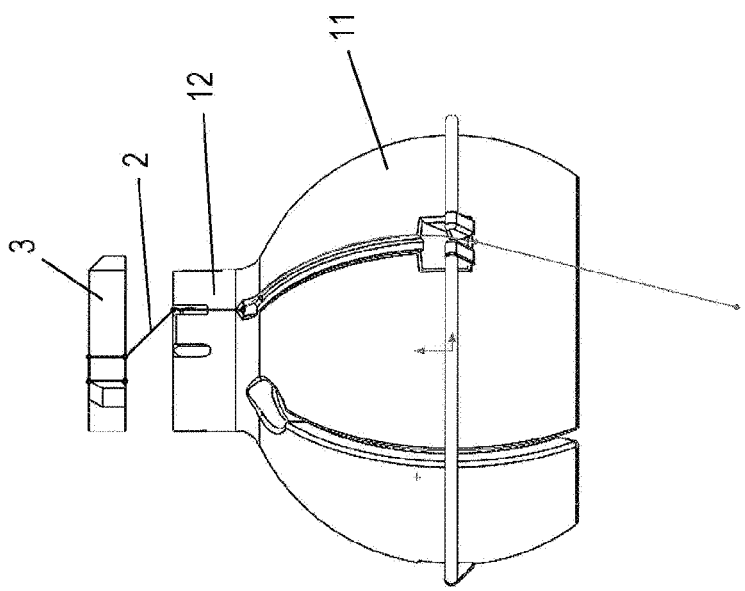
FIG. 4 shows an exploded side view of the endoscope control device when the wire is not tensioned.
Figure 5:
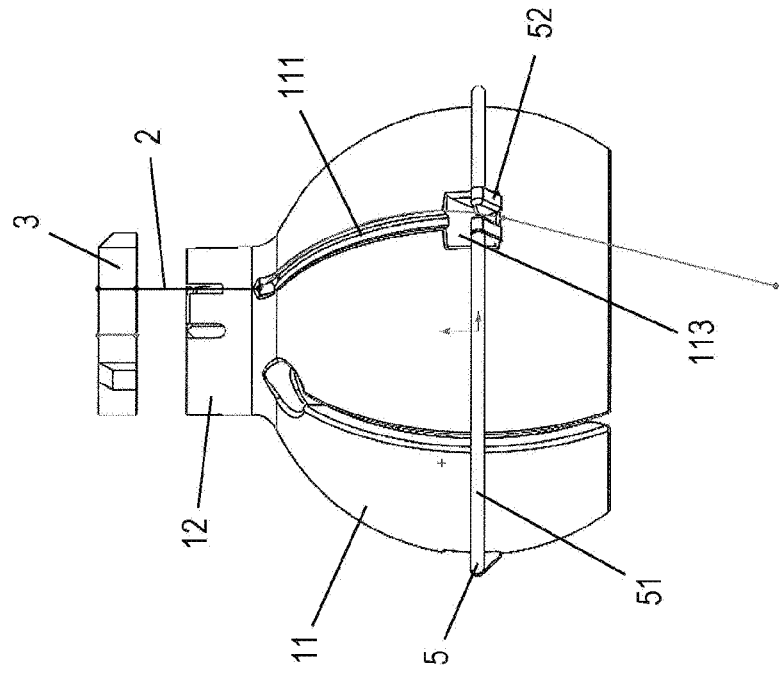
FIG. 5 shows an exploded side view of the endoscope control device when the wire is tensioned.

As it is shown in FIGS. 4 and 5, a wire 2 is anchored in each pair of through-openings 31, wherein the engagement member 4 has been omitted in FIGS. 4 and 5. Here, the wire 2 is inserted in a first pair of through-openings 31 from the distal side of the wire tensioning body 3, passes through the first through-opening 31, and is inserted into the second through-opening 31 on the proximal side of the wire tensioning body 3 and passes through the second through-opening 31. Thus, a proximal end of the wire 2 is wound along the first through-opening 31, a portion of the proximal surface of the wire tensioning body 3, the second through-opening 31 and a portion of the distal surface of the wire tensioning body 3.

In a state where the wire 2 is guided through the through-openings 31, the engagement member 4 is placed on the wire tensioning body 3. In particular, the respective locking pin 41 is inserted into its corresponding through-opening 31. Thus, the locking pin 41 clamps the wire 2 positioned in its corresponding through-hole 31.

FIG. 4 shows a position of the wire tensioning body 3 relative to the tilting body 11, where the anchored wire 2 is not tensioned. In this position, the distance between the wire insertion location on the distal surface of the wire tensioning body 3 and the wire exit location on the proximal surface of the annular extension 12 is minimal.

If the wire tensioning body 3 is rotated relative to the tilting body 11, the distance between the wire insertion location on the distal surface of the wire tensioning body 3 and the wire exit location on the proximal surface of the annular extension 12 increases. Thus, the wire 2 is tensioned as it is shown in FIG. 5.

It has to be noted that, so as to improve clarity, an exploded view is shown in FIGS. 4 and 5. In reality, the distal surface of the wire tensioning body 3 abuts against the proximal surface of the annular extension 12.

Brake Ring 5

As it is shown in FIG. 2, a brake ring 5 is placed on the outer circumference of the distal tilting body 11. More precisely, the brake ring 5 is arranged in the equatorial area of the distal tilting body 11.

The brake ring 5 is formed of an annular member 51 and a toggle lever element 52 integrally formed on the annular member 51. The toggle lever element 52 extends inwards from the annular member 51. Preferably, the toggle lever element 52 does not extend inwards from the annular member 51 perpendicularly or vertically in the median plane of the annular member 51, but the extension direction of the toggle lever element 52 from the annular member 51 is at a predetermined angle to the median plane of the annular member 51.

The end of the toggle lever element 52 facing away from the annular member 51 is seated in the opening 113 of the outer surface of the tilting body 11. The bottom of the blind-hole-like opening 113 forms an inner support surface for the toggle lever element 52. In the area of the toggle lever element 52, the annular member 51 is interrupted so as to let the wire 2 pass. The number of toggle lever elements 52 at the annular member 51 corresponds to the number of openings 113.

Due to its toggle lever element 52, the brake ring 5 can switch between two end positions. The first end position is the position in which it presses the spherical body 11 inwards against the counter ball portion (counter ball segment). This is the brake position in which a movement of the control element 1 relative to the counter ball portion is impeded by braking friction. The brake position has the purpose of locking a tilting position of the control element 1, achieved during the application of the endoscope, relative to the counter ball portion and, thus, a deflecting position of the tiltable deflecting member or deflecting portion. The second end position is the position where the brake ring 5 does not press the spherical body 11 inwards against the counter ball portion. This is the unbraked position, in which a movement of the control element 1 relative to the counter ball portion is possible.

Hood Member 6

Figure 6:
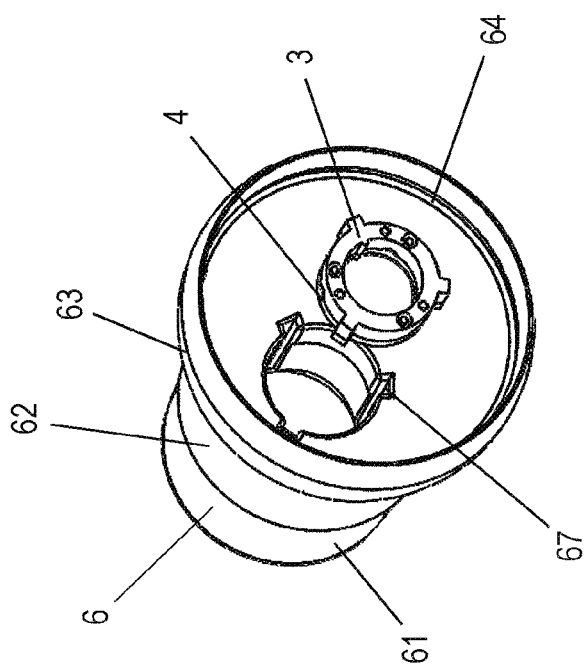
FIG. 6 shows a perspective view of a hood member of the first embodiment.

A hood member 6 is arranged on the outer side of the control element 1. FIG. 6 shows the hood member from below, i.e., from the distal side.

The hood member 6 surrounds the outer surface of the control element 1 and has a neck 61 on its proximal side and a spherical portion 63 on its distal side. A transition portion 62 is integrally arranged between the neck 61 and the spherical portion 63.

The neck 61 is constructed as a hollow cylinder, the inner diameter of which is slightly larger than the outer diameter of the wire tensioning ring 3 and the engagement member 4. On the inner circumferential side of the neck 61, three guiding grooves 67 extend in the longitudinal direction of the neck 61. The guiding grooves 67 are arranged symmetrically and equally spaced apart on the inner circumference of the neck 61. Each of the guiding grooves 67 respectively accommodates one of the protrusions 33 of the wire tensioning ring 3 and one of the protrusions 43 of the engagement member 4. Therefore, the inner shape of the guiding grooves 67 is adapted to the outer shape of the protrusions 33 of the wire tensioning ring 3 and one of the protrusions 43 of the engagement member 4. Thus, guided by the guiding grooves 67, the wire tensioning ring 3 and the engagement member 4 are able to move in the longitudinal direction of the neck 61.

The spherical portion 63 has a bell shape which is seated on the outer side of the distal tilting body 11. The spherical portion 63 is tiltable together with the distal tilting body 11, relative to the counter ball portion. In other words, the spherical portion 63 forms an outer shell that forms the bell shape and surrounds the distal tilting body 11.

Figure 8:
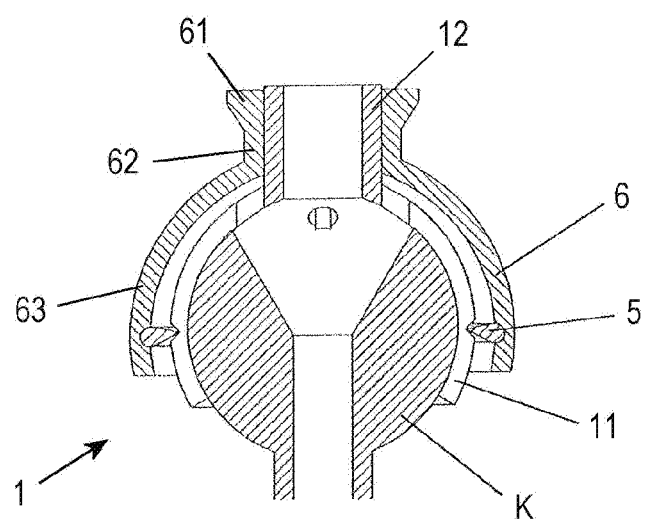
FIG. 8 shows a schematic sectional view of the control element 1 with a counter ball portion K, a tilting body 11 and a hood member 6.

Similar to the distal tilting body 11, the spherical portion 63 is a partial spherical surface body having a constant wall thickness, as it is shown in FIG. 8. Thus, the spherical portion 63 has an inner circumferential surface and an outer circumferential surface. In the assembled state of FIG. 8, the inner circumferential surface of the spherical portion 63 faces toward the distal tilting body 11 and the outer circumferential surface of the spherical portion 63 faces away from the distal tilting body 11. The inner circumferential surface of the spherical portion 63 is spaced apart from the outer circumferential surface of the distal tilting body 11 by a predetermined distance.

On the inner circumferential surface of the spherical portion 63, the hood member 6 has an annular groove 64 on the equator. The annular body 51 of the brake ring 5 is inserted into the annular groove 64. In other words, the outer circumference of the annular body 51 of the brake ring 5 abuts against the inner circumference of the annular groove 64.

The annular member 51 is placed in a tiltable manner in the annular groove 64 of the inner surface of the spherical portion 63, said annular groove being adapted to the annular shape of the annular member 51, cf. FIG. 8. The annular groove 64 forms the outer support surface of the toggle lever element 52.

Thus, the spherical portion 63 can be displaced relative to the distal tiltable body 11, by the neck 61 sliding along the outer circumference of the proximal annular extension. When the spherical portion 63 is displaced along the axis of the control element 1, relative to the distal tilting body 11, two intrinsically stable end positions are formed. When the spherical portion 63 is displaced towards the distal tilting body 11 in the distal direction, the brake position is established as first end position, cf. FIG. 8. When the spherical portion 63 is displaced away from the distal tilting body 11 in the proximal direction, the unbraked position is established as second end position.

In the completely assembled state of the control element 1, the wire tensioning ring 3 and the engagement member 4 form an assembly. This assembly has the protrusions 33 and 43 and is placed in the neck 61 of the hood member 6. Thus, in the completely assembled state of the control element 1, protrusions 33 and 43, placed in the guiding grooves 67 of the neck 61 and the assembly including the wire tensioning body 3 and the engagement member 4 are rotated by (clockwise) rotation of the hood member 6, more explicitly the neck 61, so as to tension the wires 2. The neck 61 forms a rotating member for tensioning the wires 2.

Funnel Member 7

Figure 7:
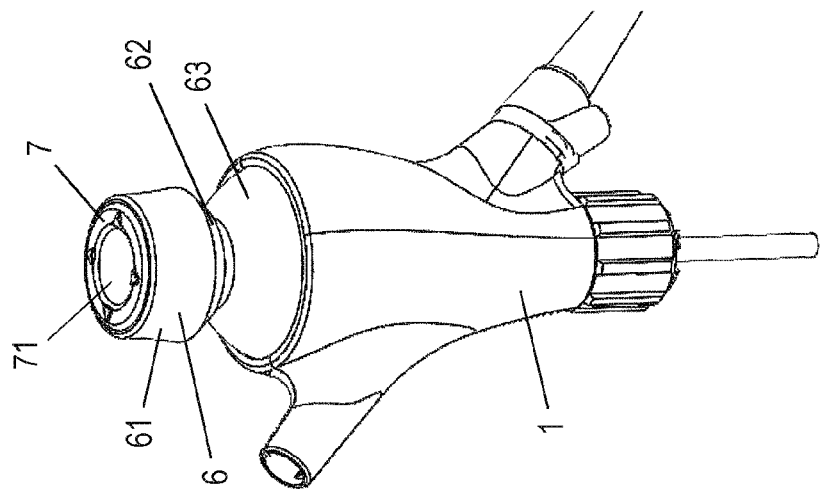
FIG. 7 shows a perspective view of the proximal end of the control element 1 with the funnel member 7 being inserted.

So as to hold the wire tensioning ring 3 and the engagement member 4 in the neck 61 of the hood member 6, a funnel member 7 is engagingly set from the proximal side of the neck 61 into the neck 61 of the hood member 6, cf. FIG. 7. Thus, the funnel member 7 prevents the wire tensioning ring 3 and the engagement member 4 from slipping out.

The funnel member 7 has a tapering funnel entrance opening 71 through which a catheter (entering tube) can be inserted from the proximal side. The funnel entrance opening 71 passes into a through-opening which is adapted to pass on the inserted catheter.

The funnel member 7 comprises a proximal portion 72 having a constantly large diameter, a distal portion 74 having a constantly small diameter, and an intermediate portion 73 having a tapering diameter integrally connecting the proximal portion 72 to the distal portion 74. The distal portion 74 comprises the through-opening for the catheter.

The funnel member 7 acts as covering body and, on the inserted outer circumference of the distal portion 74, comprises a notch 75 with which the latching nose 124 of the annular extension 12 can engage. To be more exact, two notches 75 offset by approximately 120° are formed on the outer circumference of the distal portion 74. These two notches 75 are orientated such that they can lock with the two latching noses 124 of the annular extension 12, which are offset by approximately 120°. By the funnel member 7 being held to the annular extension 12 at two points offset by approximately 120°, an extremely high stability of the control element 1 is achieved while a faulty mounting of the funnel member 7 on the annular extension 12 is avoided.

Figure 7A:
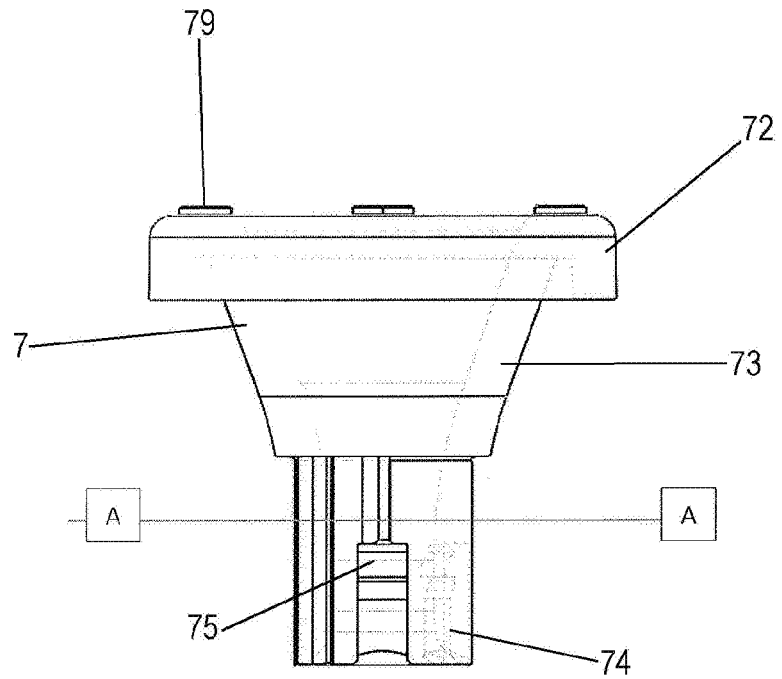
FIG. 7A shows a schematic side view of the funnel member 7.
Figure 7B:
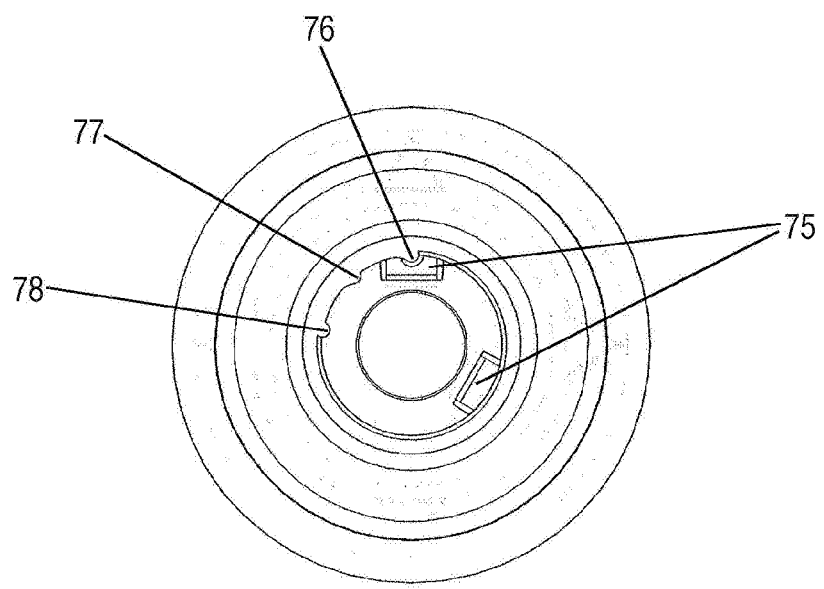
FIG. 7B shows a view from below onto the funnel member 7.
Figure 7C:
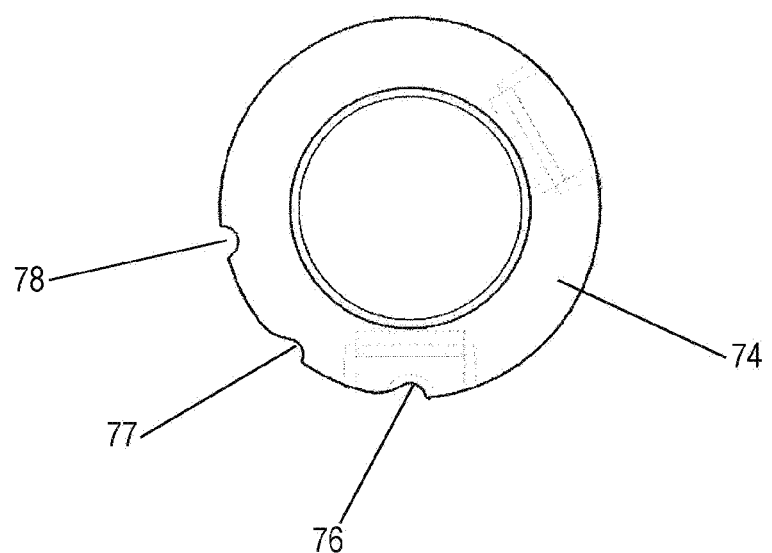
FIG. 7C shows a section along the line A-A in FIG. 7A, viewed from above.
Figure 7D:
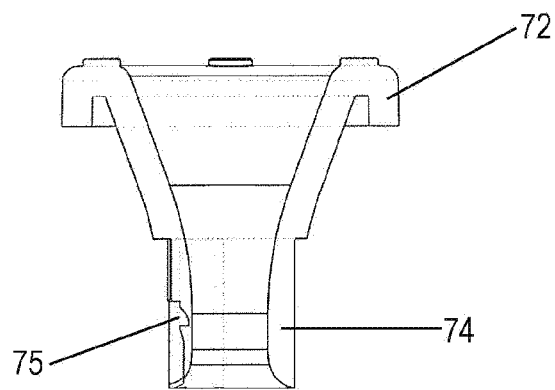
FIG. 7D shows a schematic sectional view of the funnel member 7 from the side.

On the distal portion 74 of its outer circumference, the funnel member 7 has several engagement grooves 76, 77 and 78 on the same level. To be more precise, the engagement grooves 76, 77 and 78 are in the area of the section of line A-A in FIG. 7A. FIG. 7B shows the distal portion 74 in a view from the bottom, the area of the engagement grooves 76, 77 and 78 being visible. FIG. 7C shows the section of line A-A of FIG. 7A in a view from the top.

The engagement grooves 76, 77 and 78 are constructed such that the nose 34 on the inner peripheral surface of the wire tensioning body 3 is adapted to engage in the engagement grooves 76, 77 and 78, respectively. More exactly, the construction is selected such that, in the engagement grooves 76, 77 and 78, at least one of the (or both) noses 34, 44 of the assembly composed of the wire tensioning body 3 and the engagement member 4 can engage.

The engagement grooves 76, 77 and 78 have specific shapes. On the edge being in the counter-clockwise direction in the top view of FIG. 7C, the first engagement groove 76 has a step to the outer circumference of the distal portion 74. By contrast, the transition of the first engagement groove 76 towards the edge being in the clockwise direction is flattened. The first engagement groove 76 forms a start groove. The nose/s 34 and/or 44 are/is engaged in the first engagement groove 76 when the wires 2 are not yet tensioned. Due to the specific design of the edges of the first engagement groove 76, the assembly of wire tensioning body 3 and engagement member 4 can be slightly moved out of the first engagement groove 76 in the clockwise direction, but cannot be moved in the counter-clockwise direction.

The second engagement groove 77 also has a step to the outer circumference of the distal portion 74 on the edge being in the counter-clockwise direction, and has a flattened edge to the outer circumference of the distal portion 74 in the clockwise direction. The second engagement groove 77 forms an intermediate groove.

The wires 2 can be pre-tensioned to an intermediate position by the assembly of wire tensioning body 3 and engagement member 4 being turned from the first engagement groove 76 to the second engagement groove 77 and engaging there. The wires 2 cannot be slackened (released) again from the second engagement groove 77 because, due to the step to the outer circumference of the distal portion 74, the assembly of wire tensioning body 3 and engagement member 4 cannot be turned in the counter-clockwise direction (i.e. not backwards). That is, the assembly of wire tensioning body 3 and engagement member 4 cannot be turned back from the second engagement groove 77 to the first engagement groove 76.

The third engagement groove 78 has a step to the outer circumference of the distal portion 74 on the edge located in the counter-clockwise direction and on the edge located in the clockwise direction. The third engagement groove 78 forms an end groove.

The wires 2 can be tensioned from the intermediate position to the end position by the assembly of wire tensioning body 3 and engagement member 4 being turned from the second engagement groove 77 to the third engagement groove 78 and engaging there. The wires 2 cannot be released again from the third engagement groove 78 because, due to the step to the outer circumference of the distal portion 74, the assembly of wire tensioning body 3 and engagement member 4 cannot be turned in the counter-clockwise direction (i.e. not backwards). Thus, the assembly of wire tensioning body 3 and engagement member 4 cannot be turned back from the third engagement groove 78 to the second engagement groove 77.

The engagement grooves 76, 77 and 78 are arranged on the outer circumference of the distal portion 74 above the notch 75. In other terms, the engagement grooves 76, 77 and 78 are proximal relative to the notch 75.

Preferably, on its proximal side, the funnel member 7 is provided with direction markers 79 which indicate the tilting directions of the control element 1 to the user, cf. FIG. 7. The predefined positional relation between the notches 75 on the distal portion of the funnel member 7 and the latching noses 124 of the annular extension 12 serves to ensure the correct orientation of the direction markers 79.

Assembly Method

In the following, an assembly method for the control element 1 of the first embodiment will be described.

Figure 9:
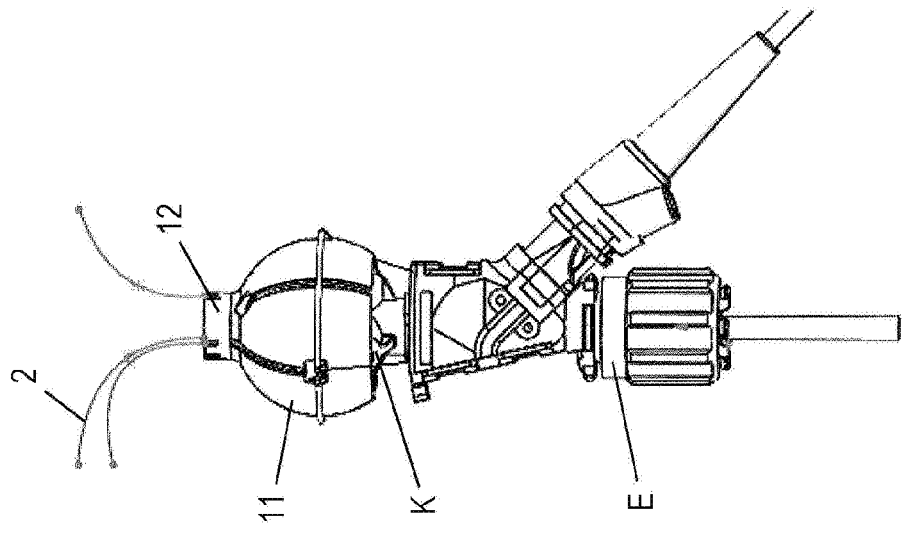
FIG. 9 shows a side view of a basic endoscope with the mounted tilting body 11.

The tilting body 11 of the control element 1 including its annular extension 12 is provided. The tilting body 11 is flexible and, due to its incisions 115, it can be bent open and placed onto a prepared counter-ball portion (counter-ball segment) of an endoscope E, cf. FIG. 9. In FIG. 9, the counter-ball portion is shown to slightly project on the distal side of the tilting body 11. In a suitable manner, this counter-ball portion is formed such that the tilting body 11 can swivel/pivot thereon as desired. The exact construction of the counter-ball portion shall not be subject to any restrictions.

Figure 10:
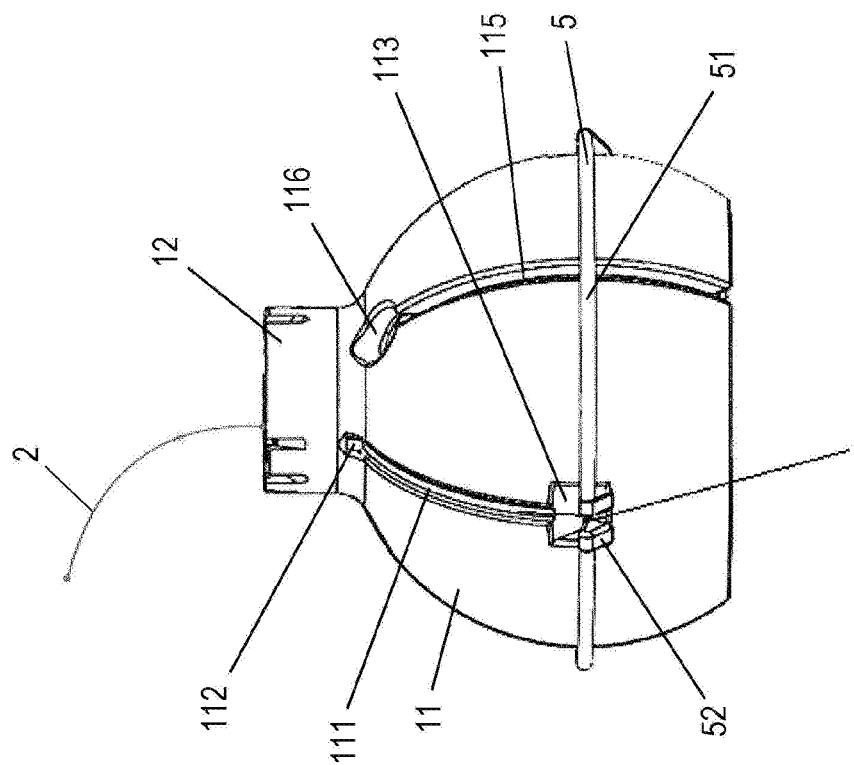
FIG. 10 shows the tilting body 11 of FIG. 9 in more detail.

Now, the brake ring 5 is set on the equator of the tilting body 11. FIG. 10 shows an enlargement of the representation of the tilting body 11 as shown in FIG. 9. It has to be noted that FIG. 10 shows the brake position. From this position, the brake ring 5 can be moved to the unbraked position in the direction shown by the arrow.

Subsequently, the wire 2 is inserted into the deflecting element (deflecting portion) on the distal end of the endoscope and is guided through the endoscope. Then, the wire 2 is guided at the outer side of the tilting body 11 from the distal side over the distal opening 113 by the toggle lever element 52 into the bottomed groove; further, the wire 2 is guided along the groove 111 from the outside through the proximal opening 112 to the inner circumferential side of the tilting body 11. Finally, the wire 2 projects from the annular extension 12, cf. FIG. 10. It can be seen in FIG. 9 that three prepared wires 2 project from the annular extension 12.

Figure 11A:
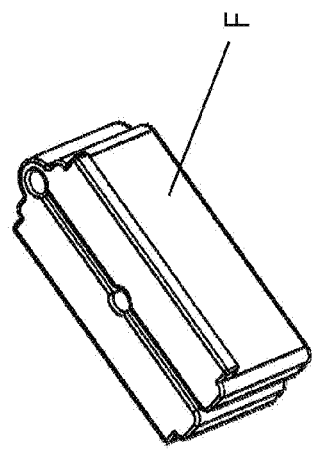
FIG. 11 shows a side view of a basic endoscope with the mounted tilting body 11 and a fixation F, FIG. 11A showing the fixation F.
Figure 11:
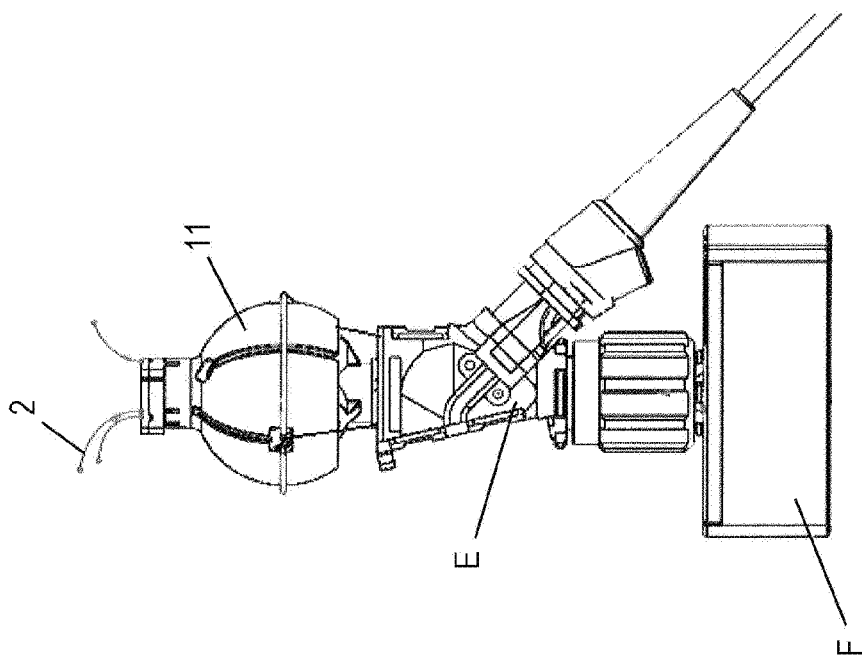

The endoscope is fixed by means of a fixation F, cf. FIG. 11. FIG. 11A shows the fixation F in more detail. The fixation F is a device for holding the endoscope, i.e. the basic endoscope E for the purpose of assembly. The fixation F comprises two clamping jaws, which are rotatable to each other and between which the basic endoscope E is held. For the purpose of fixing the basic endoscope E, every holding device adapted to maintain the basic endoscope E fixed is suited.

Figure 13:
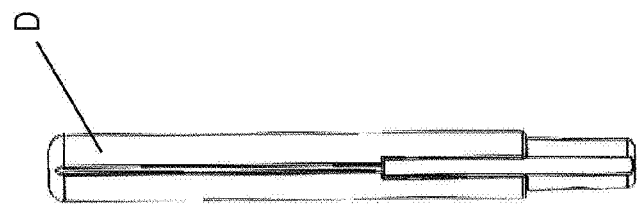
FIG. 13 shows a side view of the mounting pin D.
Figure 12:
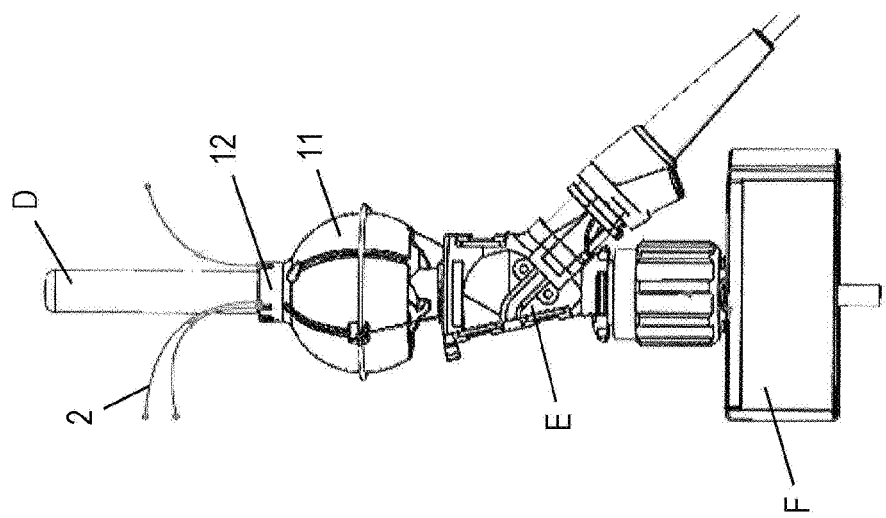
FIG. 12 shows a side view of a basic endoscope with the mounted tilting body 11 and the assembly pin D.

The wire 2 is held by hand and an assembly pin D is axially inserted from the proximal side into the annular extension 12, cf. FIG. 12. The assembly pin D is shown in FIG. 13. The assembly pin D is constructed as a solid cylindrical pin and is provided with a smaller-diameter portion and a larger-diameter portion. A stop is formed between the smaller-diameter portion and the larger-diameter portion. The assembly pin D comprises a slot extending in the axial direction, said slot extending over the smaller-diameter portion and the larger-diameter portion, as is shown in FIG. 13. To be more exact, the smaller-diameter portion of the assembly pin D is being inserted into the annular extension 12 up to the stop.

Now, the wire tensioning body 3 is mounted onto the assembly pin D such that the inner circumferential surface of the wire tensioning body 3 can slide on the outer circumferential surface of the assembly pin D and the nose 34 is guided in the slot of the assembly pin D.

Thereupon, the engagement member 4 is mounted onto the assembly pin D such that the inner circumferential surface of the engagement member 4 can slide on the outer circumferential surface of the assembly pin D and the nose 44 is guided in the slot of the assembly pin D, cf. FIG. 15. The noses 43 and 44 already determine the correct relative positions of the wire tensioning body 3 and the engagement member 4.

Figure 16A:
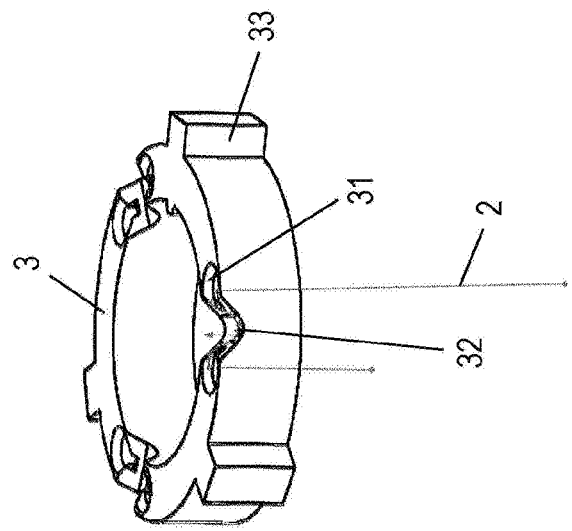
FIG. 16 shows a side view of a basic endoscope with the mounted tilting body 11 and the assembly pin D and the wire tensioning body 3, FIG. 16A showing a wire 2 inserted into the wire tensioning body 3.
Figure 16:
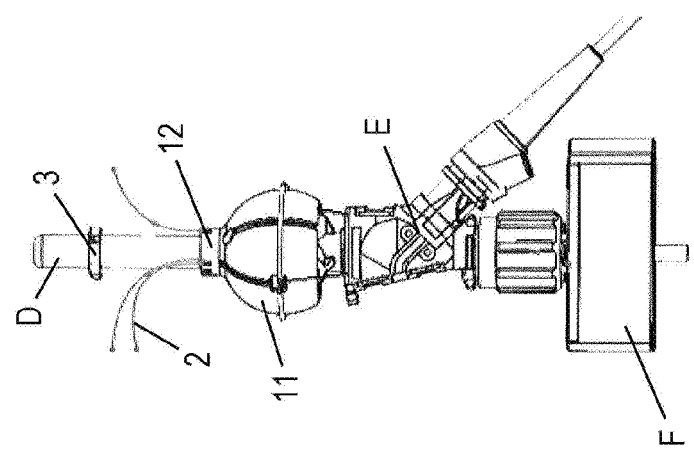

Then, the wire 2 is wound on the wire tensioning body 3 in the manner described under "fixing of the wire 2". That is to say, the wire 2 is inserted from the distal side of the wire tensioning body 3 into the first through-opening 31, passes through the first through-opening 31 in the proximal direction, and is inserted into the second through-opening 31 on the proximal side of the wire tensioning body 3, and passes through the second through-opening 31 in the distal direction, as is shown by FIG. 16.

Figure 17:
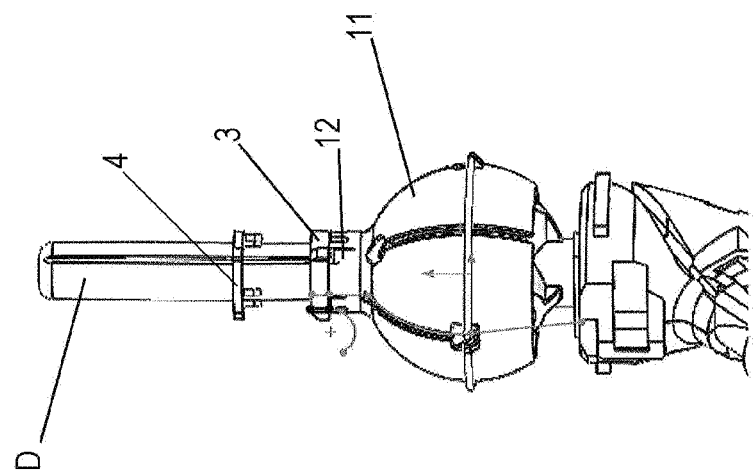
FIG. 17 shows a side view of a basic endoscope with the mounted tilting body 11 and the assembly pin D with the wire tensioning body 3 and the engagement member 4.

The wire 2 is sufficiently tensioned, with the wire tensioning body 3 being placed on the proximal surface of the annular extension 12, cf. FIG. 17.

Figure 18:
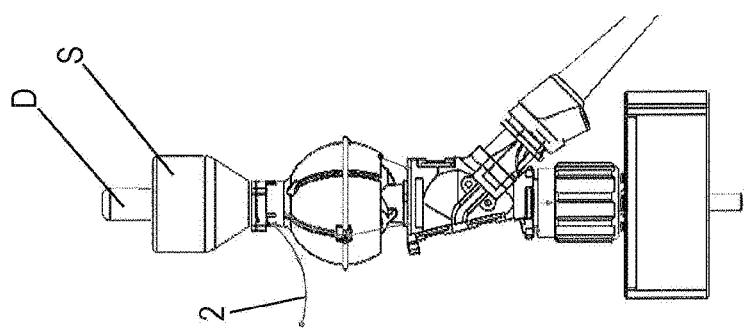
FIG. 18 shows a side view of a basic endoscope with the mounted tilting body 11 and the assembly pin D with a slider S.

Now, an adhesive is applied onto the proximal surface of the wire tensioning body 3 and the engagement member 4 is pushed to the proximal surface of the wire tensioning body 3 by means of a slider S by the respective locking pins 41 being inserted into the corresponding through-openings 31 and the bulges 42 penetrating into the notches 32, cf. FIG. 18.

Figure 20:
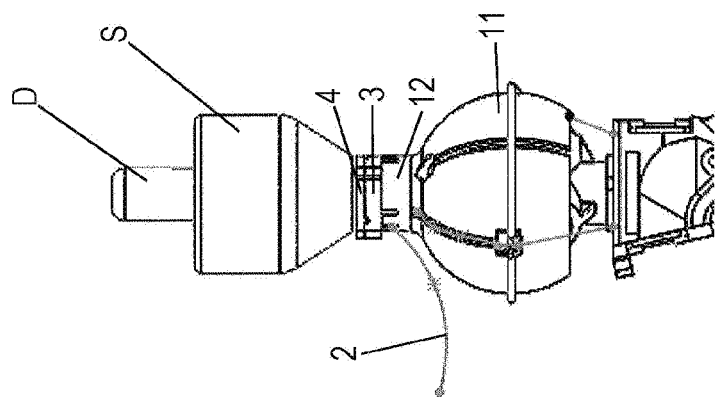
FIG. 20 shows a side view of a basic endoscope with the mounted tilting body 11 and the assembly pin D with the slider S.
Figure 19:
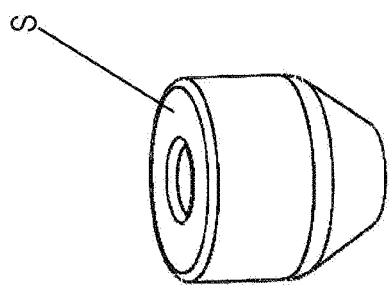
FIG. 19 shows a perspective view of the slider S.

The slider S is shown more clearly in FIG. 19. The slider S is a hollow cylinder which is provided with a tapering and which is adapted to slide on the assembly pin D and having, on the tapering, a surface by which the slider S pushes the engagement member 4 to the wire tensioning body 3, cf. FIG. 20.

Figure 21:
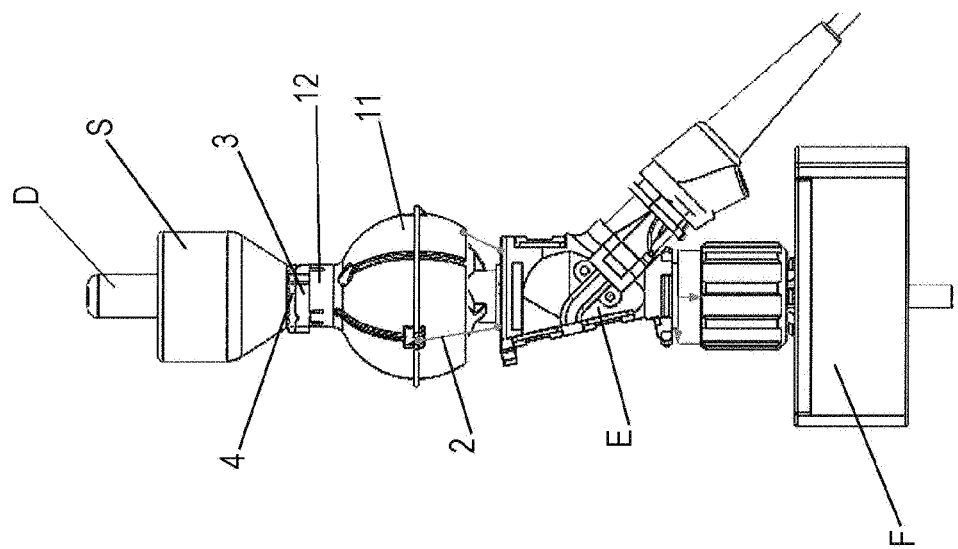
FIG. 21 shows a side view of a basic endoscope with the mounted tilting body 11 and the assembly pin D with the slider S.

The excess part of the wire 2 projecting at the wire tensioning body 3 is cut off, cf. FIG. 21.

Figure 22:
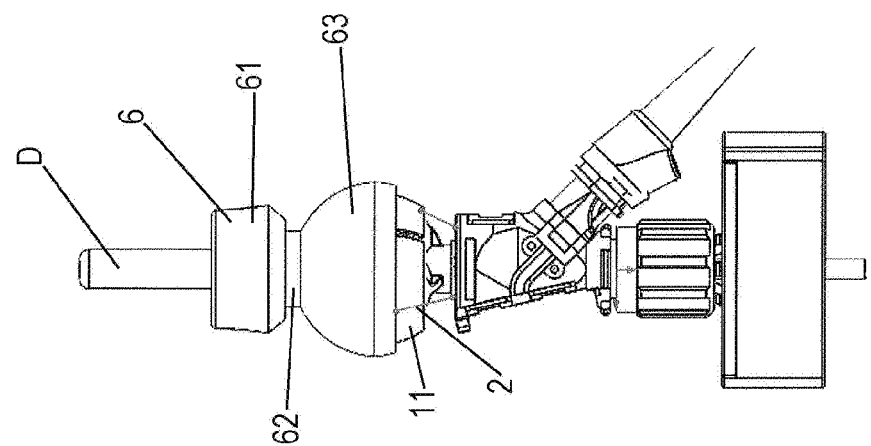
FIG. 22 shows a side view of a basic endoscope with the mounted tilting body 11 and the assembly pin D and an assembled hood member 6.

The slider S is removed and, in its stead, the hood member 6 is placed on the proximal side of the control element 1 with its spherical portion 63 up front such that the protrusions 33, 43 of the engagement member 4 and the wire tensioning body 3 are arranged in the guiding groove 67 and the annular member 51 is seated in the annular groove 64, cf. FIG. 22.

Figure 23:
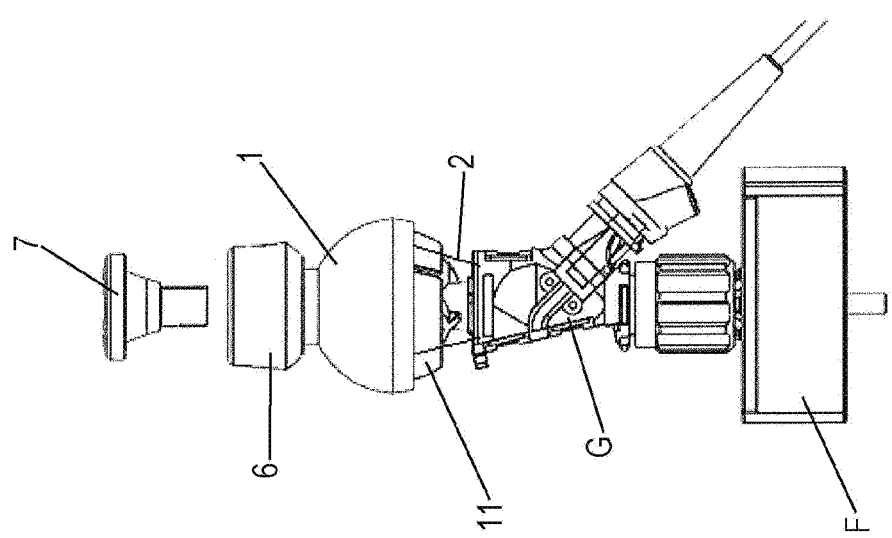
FIG. 23 shows a side view of a basic endoscope with the mounted tilting body 11 and the assembled hood member 6, the funnel member 7 being assembled.

The assembly pin D is pulled out and, in its stead, the funnel member 7 is inserted at the proximal side of the control element 1 until it engages with the latching nose 124, cf. FIG. 23. In this position, the nose 34 and/or 44 are/is engaged in the first engagement groove 76 of the funnel member 7.

Figure 24:
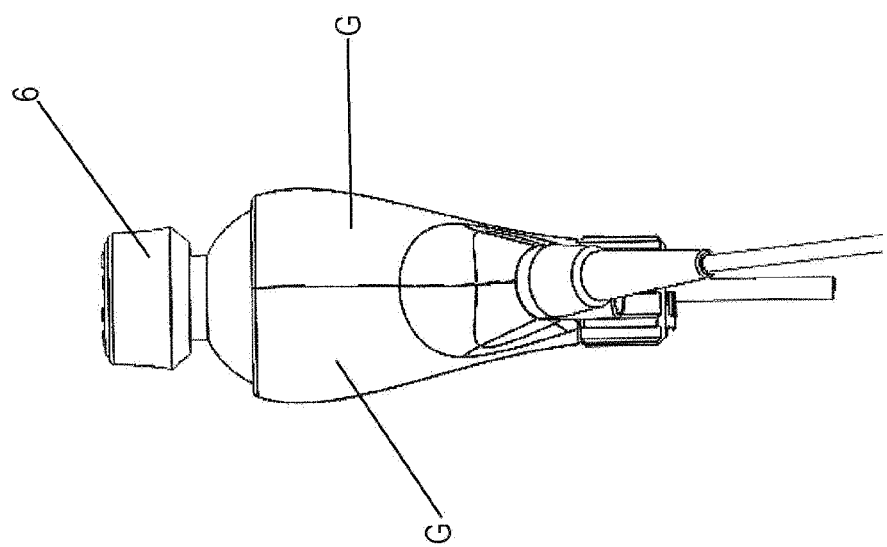
FIG. 24 shows a side view of a basic endoscope with mounted housing parts G.

The fixation F is removed and housing parts are placed on the control element 1, as is shown in FIG. 24.

Thus, the assembly of the control element 1 is completed. The control element 1 is ready for tensioning the wires 2.

Advantages of the Control Element 1

The control element 1 of the first embodiment is easy to operate. The user intending to tension the wires rotates the neck 61 of the hood member 6 in the predetermined direction (here: clockwise) by the predetermined path of rotation, which is determined by the engagement grooves 76, 77, 78, until the assembly of wire tensioning ring 3 and engagement member 4 engages in the intermediate groove 77 or the end groove 78. The engagement of the assembly of the wire tensioning ring 3 and the engagement member 4 in the end groove 78 is irreversible. Once a wire has been tensioned, this cannot be reversed. Thus, the user cannot inadvertently change an endoscope that has been brought into the application state by tensioning the wires, into the untensioned-wire state. Thus, an endoscope comprising this control element 1 is very safe in application.

As the assembly of wire tensioning ring 3 and engagement member 4 is adapted to engage in the intermediate groove 77 or the end groove 78, the tensions of the wires 2 can be differently strong. That is, by engagement of the assembly of wire tensioning ring 3 and engagement member 4 in the intermediate groove 77, the wires 2 are tensioned less strongly; this results in a less hard tensioning of the wires. By engaging the assembly of wire tensioning ring 3 and engagement member 4 in the end groove 78, the wires 2 are tensioned more strongly; this results in a very hard wire tensioning.

The intermediate groove 77 can be used to achieve a momentary work tension of the wires 2. Should, after a certain period of time, the tension of the wires have slackened and not be sufficient any more despite the engagement of the assembly of wire tensioning ring 3 and engagement member 4 in the intermediate groove 77, the assembly of wire tensioning ring 3 and engagement member 4 can be turned on from the intermediate groove 77 to the end groove 78 and engage therein so as to again achieve a suitable wire tension.

By the assembly of wire tensioning ring 3 and engagement member 4 engaging in the engagement grooves 76, 77, 78, the wires 2 can be made to reach an exactly predefined tension.

The tensioning of the wires is realized by a rotational movement taking place about the longitudinal axis of the hood member 6. The temporary locking of the wires by the brake ring 5 is realized by a sliding movement taking place in the axial direction (a translational motion) of the hood member 6. Thus, completely different procedures are required for tensioning the wires and for temporarily locking the wires. Thus, the tensioning of the wires and the temporary locking of the wires take place completely separately from each other.

The control element 1 can be designed as a disposable component. Its individual parts consist of plastic, for example. Its manufacture and assembly is easy and inexpensive.

Second Embodiment

Below, a second embodiment of the present invention will be described by means of the attached FIGS. 25 and 26.

Figure 25:
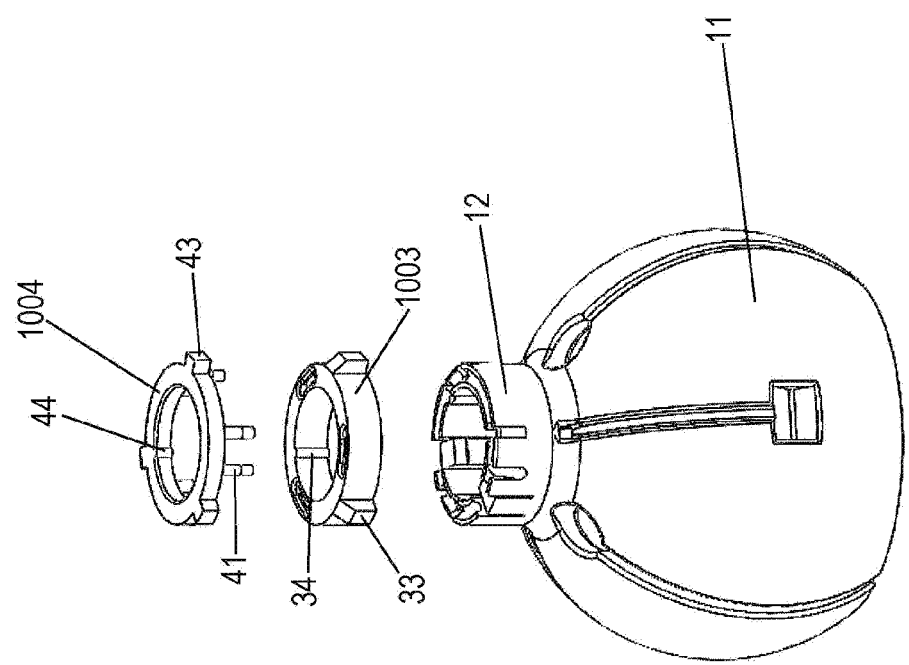
FIG. 25 shows a perspective exploded view of a control element of the second embodiment of the present invention.
Figure 26:
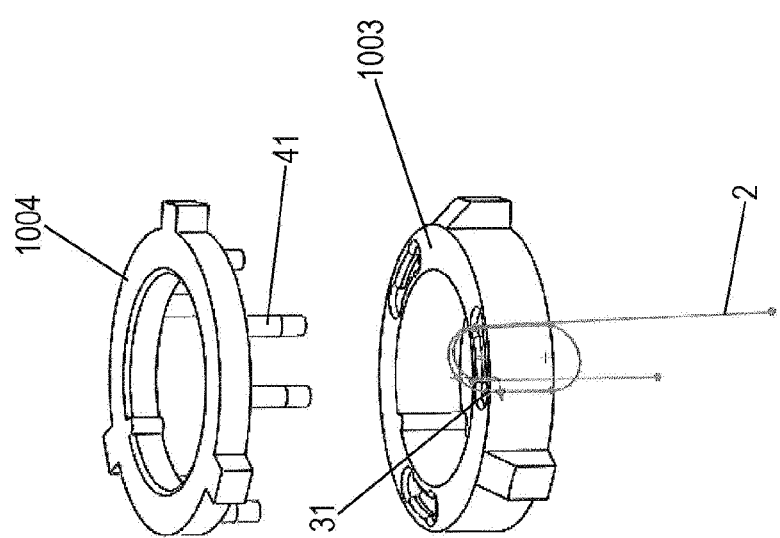
FIG. 26 shows the wire tensioning body 1003 and the engagement member 1004 of the second embodiment.

The second embodiment differs from the first embodiment such that the wire tensioning body 1003 does not have any notches and the engagement member 1004 does not have any noses, cf. FIGS. 25 and 26.

So as to nevertheless achieve a sufficient tensioning and fixing of the wire 2, the wire 2 is inserted from the distal side of the wire tensioning body 1003 into the first one of a pair of through-openings 31, passes through the first through-opening 31 in the proximal direction, is inserted into the second through-opening 31 at the proximal side of the wire tensioning body 1003, and passes through the second through-opening 31 in the distal direction. Subsequently, the wire 2 is again inserted into the first one of the pair of through-openings 31 in the proximal direction, passes through the same in the proximal direction, and is reinserted into the second through-opening 31 at the proximal side of the wire tensioning body 1003, and again passes through the second through-opening 31 in the distal direction, cf. FIG. 26. Thus, the wire 2 runs in two loops in the wire tensioning body 1003.

Therefore, for the assembly, the adhesive is applied on the proximal surface of the wire tensioning body 1003, and the engagement member 1004 is displaced to the proximal surface of the wire tensioning body 1003 by a slider S by the respective locking pins 41 being inserted into the corresponding through-openings 31.

As for the rest, the second embodiment is equal to the first embodiment.

Third Embodiment

Below, a third embodiment of the present invention will be described by means of the attached FIGS. 27 and 28.

The third embodiment differs from the first embodiment in that the individual wires 2, 2A are adapted to be tensioned differently whereas all wires 2 of the first embodiment are evenly tensioned. As for the rest, the third embodiment is equal to the first embodiment.

Figure 27:
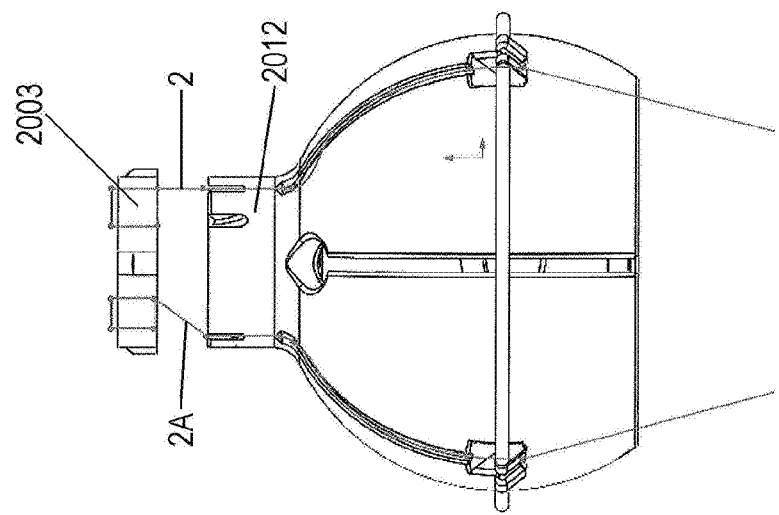
FIG. 27 shows an exploded side view of a control element of the third embodiment of the present invention; here, a position with untensioned wires is shown.

As is shown by FIG. 27, a distal tilting body 11 with its proximal annular extension 2012 is combined with a wire tensioning body 2003 such that a first wire 2 is perpendicularly arranged from the wire tensioning body 2003 to the annular extension 2012 while a second wire 2A is arranged obliquely from the wire tensioning body 2003 to the annular extension 2012. In particular, the second wire 2A obliquely runs from the annular extension 2012 to a through-opening 31, which is arranged closer to the through-openings 31 for the first wire. Thus, the tensionable path distance of the first wire 2 is shorter than that of the second wire 2A.

Figure 28:
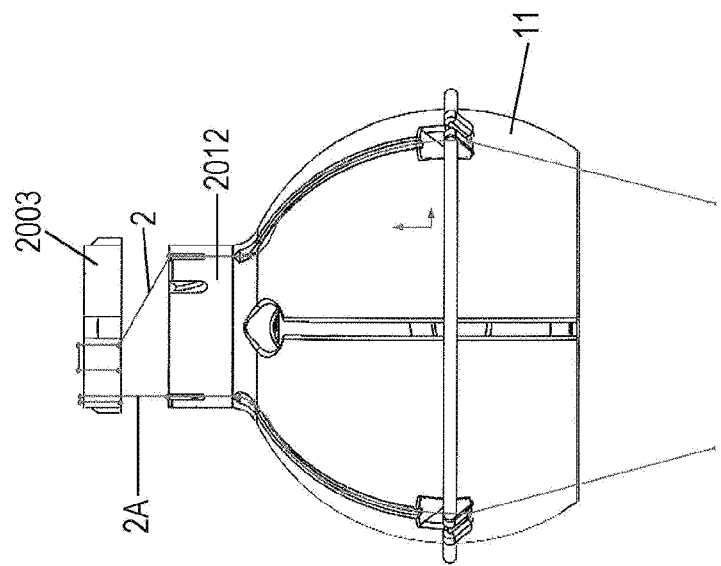
FIG. 28 shows an exploded side view of the control element of the third embodiment; here, a position with tensioned wires is shown.

The wires 2, 2A are tensioned by turning the wire tensioning body 2003 from the position shown in FIG. 27 such (to the left) that the first wire 2 is tensioned by the wire tensioning body 2003 to the left, while the second wire 2A is first released to the left and is then, upon further turning of the wire tensioning body 2003, also tensioned to the left; it is, however, tensioned less strongly than the first wire 2, cf. FIG. 28.

Due to the known geometries, it can be exactly calculated, in the principle of the third embodiment, by which amount the first wire 2 is tensioned more strongly than the second wire 2A.

Differently tensioned wires entail the following advantage. When the introductory tube (catheter) of the endoscope in its resting state or also when applied is usually wound twice or several times about its own axis, the wires in the endoscope are exposed to different tensions. Therefore, in most cases, one wire is tensioned more strongly than the other wires. In this way, the control element (joystick) is already tilted in its start position in a direction in which it is pulled by the more strongly tensioned wire. To make up for this, the present embodiment provides a solution according to which, despite the winding about its own axis, the endoscope is applicable such that the control element (joystick) in its inoperative state is in the vertical neutral position. This makes it easier to use the endoscope. The user no longer has to consider pretensionings of the wire caused by winding about its own axis or, at least, he has to consider these less.

As the exact type of the windings of the introductory tube (catheter) of the endoscope about its own axis is usually known, it is also possible to specify the wire that is exposed to a stronger tension.

Fourth Embodiment

Below, a fourth embodiment of the present invention will be described by means of the attached FIG. 29.

In the third embodiment, wires are tensioned differently due to having differently long tensionable distances between the annular extension and the wire tensioning body. In the fourth embodiment, wires are tensioned differently by using an inner through-opening 3031 and an outer through-opening 3032 on the wire tensioning body 3003. The distance of the inner through-opening 3031 to the center of the wire tensioning body 3003 is less than the distance of the outer through-opening 3032 to the center of the wire tensioning body 3003.

One wire 2 is inserted into the inner through-opening 3031 and into the outer through-opening 3032, respectively, is guided to the inner circumference of the wire tensioning body 3003, is guided in the distal direction and is, in the distal direction, again inserted into the respective inner through-opening 3031 or outer through-opening 3032; thus, every wire forms a whole loop. Alternatively, one wire 2 is inserted into the inner through-opening 3031 and into the outer through-opening 3032, respectively, and is clamped therein by one locking pin of the engagement member, respectively, without forming a loop.

Figure 29A:
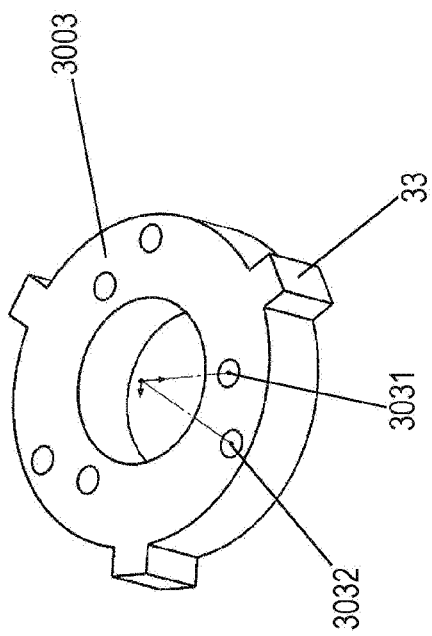
FIG. 29A shows the wire tensioning body 3003 of the fourth embodiment.
Figure 29:
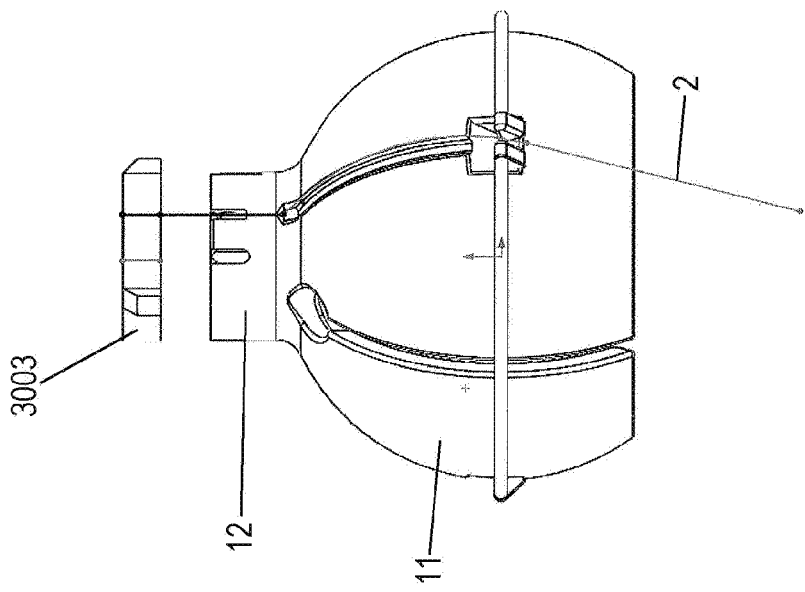
FIG. 29 shows an exploded side view of a control element of the fourth embodiment of the present invention.

For tensioning the wires, the wire tensioning body 3003 is turned clockwise from the position shown in FIG. 29, the wire clamped in the inner through-opening 3031 being tensioned less strongly than the wire clamped in the outer through-opening 3032.

Due to the known geometries, also in the case of the principle of the fourth embodiment, the exact amount by which the one wire is tensioned more strongly than the other wire can be calculated. This entails an advantage similar to that of the third embodiment.

Alternatives

In the present embodiment, three wires 2 are provided as pulling cables. The number of wires 2 is not limited here. One wire, 2, 3, 4 or more wires can be provided. If two or more wires 2 are provided, the respective grooves 111 are arranged at even distances to each other, perpendicularly to the equator of the tilting body 11.

In the embodiments, the wire 2 is only clamped on the wire tensioning body 3 by the wire 2 being guided through the through-openings 31 and the respective locking pin 41 being inserted into its pertinent through-opening 31. Thus, the locking pin 41 clamps the wire 2, which is located in its pertinent through-opening 31.

When anchoring the wire 2 on the wire tensioning body 3, the wire 2 can alternatively or additionally be inserted from the distal side of the wire tensioning body 3 into a first one of the pair of through-openings 31, pass through the first through-opening 31, and be inserted into the second through-opening 31 on the proximal side of the wire tensioning member 3, pass through the second through-opening 31, and then be linked to the portion of the wire 2 on the distal side of the wire tensioning member 3. As a further alternative, the wire 2 can comprise a crimped portion which is e.g. arranged below the second through-opening 31 and is deformed such that the deformed crimped portion cannot pass through the through-opening 31 blocked by the locking pin 41.

In the embodiments, the wire 2 can be pulled by hand for the assembly. So as to increase the mounting precision, a wire-pulling means can be used for pulling and tensioning the wire 2 at an adjustable force. In the first embodiment, the wire 2 can be pulled at 2 Newton. In the second embodiment, the wire 2 can be pulled at 3 Newton. Of course, these are only examples. Other forces may be applied.

The adhesive agent, which is applied onto the proximal surface of the wire tensioning body 3 when the engagement member 4 and the wire tensioning body 3 are assembled, may be omitted.

In the embodiments, the annular extension 12 is provided with two latching noses 124 displaced by 120° and adapted to engage in the respective notches 75 displaced by 120° and formed on the distal portion of the funnel member 7. As an alternative, the annular extension 12 can be provided with only one latching nose 124 adapted to engage in one single notch 75 formed on the distal portion of the funnel member 7. As an alternative, the annular extension 12 can be provided with three or more latching noses that are adapted to engage with respective three or more notches 75 formed on the distal portion of the funnel member 7. When two latching noses 124 are provided, these can also be arranged to be diagonally opposite to each other. Analogously, then, two notches are formed diagonally opposite on the distal portion of the funnel member 7.

The second engagement groove 77 as intermediate groove can have a flattened edge to the outer circumference of the distal portion 74 in the counter-clockwise direction and in the clockwise direction. Thus, the second engagement groove 77 can allow a reversible engaging of the assembly of wire tensioning body 3 and engagement member 4. In this alternative, wires 2 can be tensioned by the assembly of wire tensioning body 3 and engagement member 4 being turned from the first engagement groove 76 to the second engagement groove 77 and engaging there. The wires 2 can be slackened (released) again by the assembly of wire tensioning body 3 and engagement member 4 being turned from the second engagement groove 77 to the first engagement groove 76 and engaging there.

The second engagement groove 77 can be omitted. In this alternative, the wires 2 can only be tensioned by engagement in the third engagement groove 78.

In a further alternative, the second engagement groove 77 and/or the third engagement groove 78 can also have, instead of the step, a flattened edge to the outer circumference of the distal portion 74 in the counter-clockwise direction as well. A control element constructed in this way allows a reversible engagement of the assembly of wire tensioning body 3 and engagement member 4 in the second engagement groove 77 and/or third engagement groove 78. Thus, the wires can be tensioned and, if required, again be slackened by the user.

In the embodiments, the wire guiding groove 111 is designated as wire guiding means. Within the terms of the invention, the wire guiding means is not restricted to the groove 111 and comprises any member on the control element 1 which serves to guide the wire 2. Thus, another possibility could be a modification according to which the groove 111 is omitted and the wire 2 is only guided in the proximal annular extension 12.

LIST OF REFERENCE SIGNS 1 control element
2 wire
2A wire
3 wire tensioning body
4 engagement member
5 brake ring
6 hood member
7 funnel member
11 distal tilting body
12 proximal annular extension 31 wire anchoring openings
32 notch
33 protrusion
34 nose
41 locking pin
42 bulge
43 protrusion
44 nose
51 annular member
52 toggle lever element
61 neck
62 transition portion
63 spherical portion
64 annular groove
67 guiding groove
71 funnel entrance opening
72 proximal portion
73 intermediate portion
74 distal portion
75 notch
76 engagement groove
77 engagement groove
78 engagement groove
79 direction marker
111 wire guiding means, groove
112 top opening, proximal opening
113 bottom opening, distal opening
115 incision
116 end portion
121 channel
122 wire inlet slit
123 wire outlet slit
124 latching nose for covering body
1003 wire tensioning body
1004 engagement member
2003 wire tensioning body
2011 distal tilting body
2012 proximal annular extension
3003 wire tensioning body
3031 inner through-opening
3032 outer through-opening
D assembly pin
E endoscope
F fixation
G housing
K counter-ball portion
S slider

The invention claimed is:

1. An endoscope control device for a non-rigid endoscope, comprising:
   a tiltable control element for effecting a deflection movement via a transmission wire, the control element including a wire guide for guiding a wire, the wire being arranged at the control element on the wire guide for realizing the deflection movement;
   at least one engagement groove;
   at least one nose; and
   a wire tensioning body in which a proximal end of the wire is anchored and which is movable relative to the control element for changing the tension of the wire between the wire guide and the wire tensioning body,
   wherein:
   the wire guide comprises one of the at least one engagement groove or the at least one nose, and
   the at least one engagement groove and the at least one nose engage with each other at a predefined length of movement of the wire effected by the rotating movement of the wire tensioning body.

2. The endoscope control device according to claim 1, wherein
   the wire tensioning body is movable relative to the control element such that a predefined tension can be applied to the wire.

3. The endoscope control device according to claim 2, wherein
   the wire tensioning body is rotatable relative to the control element such that the predefined tension can be applied to the wire.

4. Endoscope control device according to claim 1, wherein
   the at least one engagement groove and the at least one nose are designed to be engageable such that the engagement is irreversible.

5. The endoscope control device according to claim 1, wherein
   the at least one engagement groove and the at least one nose are designed to be engageable so that the engagement can be released.

6. The endoscope control device according to claim 1, wherein
   the wire tensioning body is arranged at the proximal side of the control element.

7. The endoscope control device according to claim 1, wherein
   the wire tensioning body is an annular body having wire anchoring openings in which the wire is seated, the annular body being rotatable relative to the control element for tensioning the wire.

8. The endoscope control device according to claim 7, wherein
   the annular body is arranged with respect to the control element such that a proximal surface of the annular body faces away from the control element and a distal surface of the annular body faces towards the control element,
   the wire anchoring openings are through-holes between the proximal surface and the distal surface of the annular body, and,
   for anchoring, the proximal end of the wire is wound along a first wire anchoring opening, a portion of the proximal surface of the annular body, a second wire anchoring opening, and a portion of the distal surface of the annular body.

9. The endoscope control device according to claim 1, wherein,
   in the wire tensioning body, at least two wires are anchored in wire anchoring openings such that the at least two wires have tensionable lengths differently long to each other between their respective anchoring site at the wire tensioning body and their respective wire guide of the control element, wherein, during a movement of the wire tensioning body relative to the wire guide of the control element, the at least two anchored wires are tensionable at changes in length which are different from each other.

10. The endoscope control device according to claim 1, wherein a brake ring is provided on the outer circumference of the tiltable control element and is moveable in an axial direction of the tiltable control element for temporarily locking the wire independent of the wire tensioning body.

11. The endoscope control device according to claim 1, wherein the tiltable control element comprises a tilting body having an extension extending in proximal direction from the tilting body,
    wherein the tilting body comprises a hollow ball portion seated on a counter ball portion.

12. An endoscope comprising an endoscope control device according to claim 1.

\* \* \* \* \*